United States Patent
May

(10) Patent No.: US 8,313,490 B2
(45) Date of Patent: Nov. 20, 2012

(54) SINGLE PLANE ANATOMIC REFERENCING TISSUE PREPARATION

(75) Inventor: Justin J. May, Leesburg, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 956 days.

(21) Appl. No.: 11/687,161

(22) Filed: Mar. 16, 2007

(65) Prior Publication Data

US 2008/0234683 A1     Sep. 25, 2008

(51) Int. Cl.
*A61F 5/00*     (2006.01)
*A61B 17/56*    (2006.01)

(52) U.S. Cl. ........................................................ 606/87
(58) Field of Classification Search .................... 606/80, 606/86 R, 87, 88, 89, 96
See application file for complete search history.

(56) References Cited

U.S. PATENT DOCUMENTS

| | | | | |
|---|---|---|---|---|
| 4,457,307 A | * | 7/1984 | Stillwell | 606/88 |
| 5,474,559 A | * | 12/1995 | Bertin et al. | 606/89 |
| 5,486,180 A | * | 1/1996 | Dietz et al. | 606/87 |
| 5,653,714 A | * | 8/1997 | Dietz et al. | 606/87 |
| 5,709,689 A | * | 1/1998 | Ferrante et al. | 606/86 R |
| 5,908,424 A | * | 6/1999 | Bertin et al. | 606/88 |
| 6,056,754 A | * | 5/2000 | Haines et al. | 606/80 |
| 6,554,838 B2 | * | 4/2003 | McGovern et al. | 606/87 |
| 6,575,980 B1 | * | 6/2003 | Robie et al. | 606/88 |
| 6,966,731 B2 | * | 11/2005 | VanderPol et al. | 409/179 |
| 7,255,702 B2 | * | 8/2007 | Serra et al. | 606/80 |
| 7,462,199 B2 | * | 12/2008 | Justin et al. | 623/20.34 |
| 7,481,814 B1 | * | 1/2009 | Metzger | 606/87 |
| 7,488,324 B1 | * | 2/2009 | Metzger et al. | 606/89 |
| 7,510,557 B1 | * | 3/2009 | Bonutti | 606/86 R |
| 7,615,054 B1 | * | 11/2009 | Bonutti | 606/88 |
| 7,766,913 B2 | * | 8/2010 | Bennett et al. | 606/86 R |
| 7,794,462 B2 | * | 9/2010 | May et al. | 606/79 |
| 8,052,687 B2 | * | 11/2011 | Sackett et al. | 606/80 |
| 2006/0293682 A1 | * | 12/2006 | Justin et al. | 606/88 |
| 2008/0234664 A1 | | 9/2008 | May et al. | |
| 2008/0234683 A1 | * | 9/2008 | May | 606/87 |

* cited by examiner

*Primary Examiner* — Kevin T Truong
*Assistant Examiner* — Christopher Beccia
(74) *Attorney, Agent, or Firm* — Schwegman, Lundberg & Woessner, P.A.

(57) ABSTRACT

A system for preparing a surface of an anatomical structure, such as a bone or cartilage, for example, to receive an orthopaedic implant. The system includes a surgical instrument for preparing the surface and a guide engageable with a follower of the surgical instrument. The guide includes a track or path configured to guide the follower and prepare a desired surface on the anatomical structure. The guide facilitates guidance of the surgical instrument in two dimensions.

21 Claims, 3 Drawing Sheets

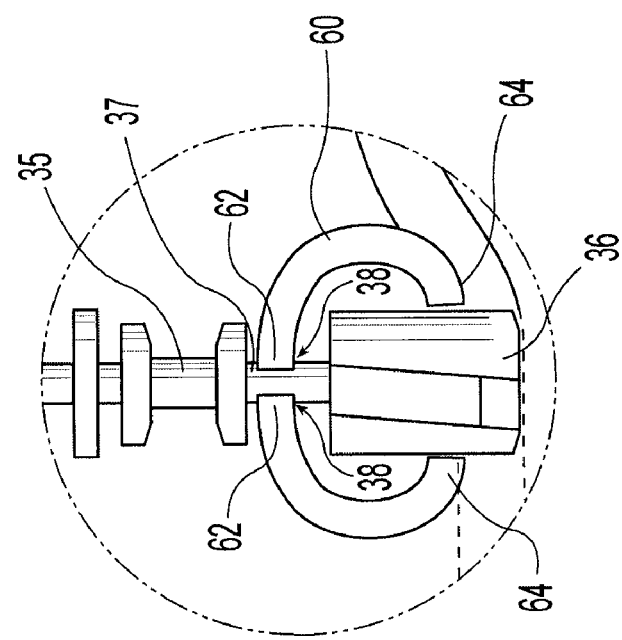
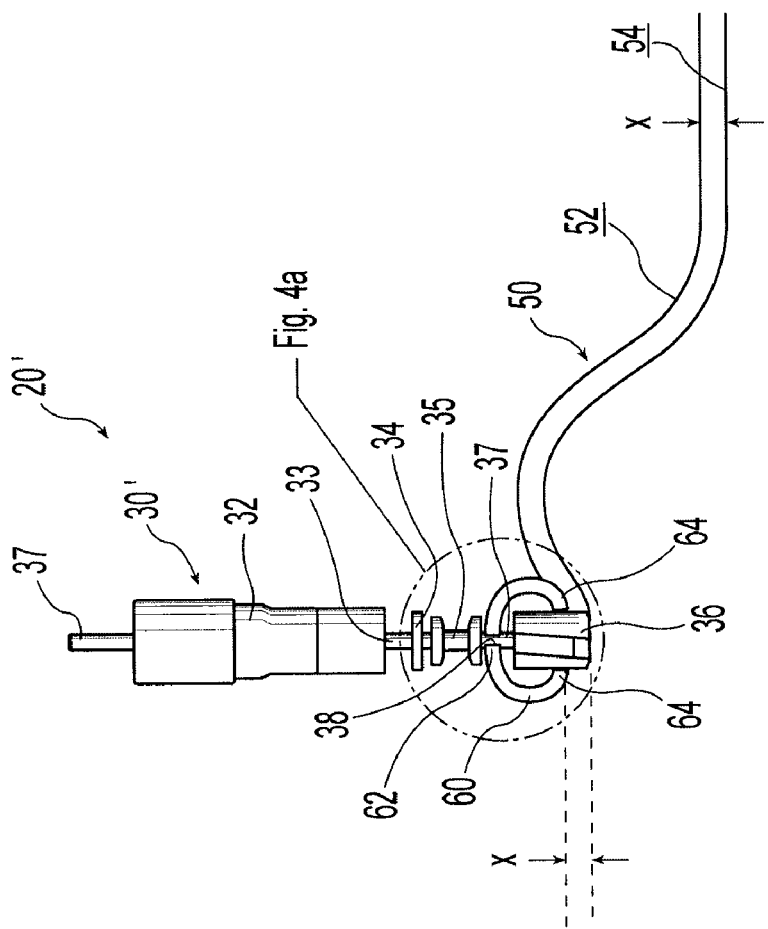
Fig. 4a
Fig. 4

SINGLE PLANE ANATOMIC REFERENCING TISSUE PREPARATION

BACKGROUND

1. Field of the Invention

The present invention relates to surgical guides utilized for preparing a surface of an anatomical structure, such as a bone or cartilage, for example, to receive an orthopaedic implant. More particularly, the present invention relates to a system for preparing a surface of an anatomical structure to receive an orthopaedic implant using a guide which facilitates preparation of the anatomical surface in two dimensions.

2. Description of the Related Art

Implantation procedures for orthopaedic implants typically require a surface of an anatomical structure to be prepared to receive the orthopaedic implant. Such surface preparation is typically done with highly accurate techniques.

SUMMARY

The present invention provides a system for preparing a surface of an anatomical structure, such as a bone or cartilage, for example, to receive an orthopaedic implant. The system includes a surgical instrument for preparing the surface and a guide engageable with a follower of the surgical instrument. The guide includes a track or path configured to guide the follower and prepare a desired surface on the anatomical structure. Advantageously, the guide facilitates guidance of the surgical instrument in two dimensions.

In one form thereof, the present invention provides a system for preparing a surface of an anatomical structure, including a surgical instrument, the surgical instrument including a follower; and a guide connected to the anatomical structure and engageable with the follower, the guide comprising a track configured to guide the follower in two dimensions when the follower is engaged with the guide.

In another form thereof, the present invention provides a system for preparing a surface of an anatomical structure, including a surgical instrument; and guide means for guiding the surgical instrument in two dimensions.

In yet another form thereof, the present invention provides a method for preparing a surface of an anatomical structure in two dimensions, including the steps of providing a guide having a track; engaging a follower of a surgical instrument with the track; and guiding preparation of the surface in two dimensions by moving the follower in the track.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 4 is a perspective view of a system according to another embodiment, further illustrating a secondary guide; and FIG. 4a is a close-up view of a portion of the system of FIG. 4.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION

Figure 1:
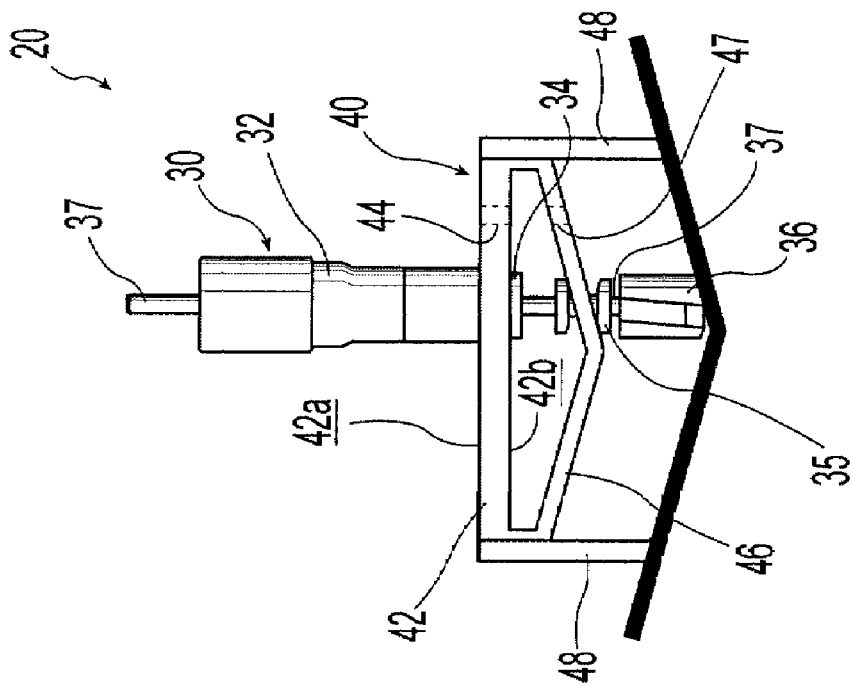
FIG. 1 is a perspective view of a system according to one embodiment of the present invention.
Figure 2:
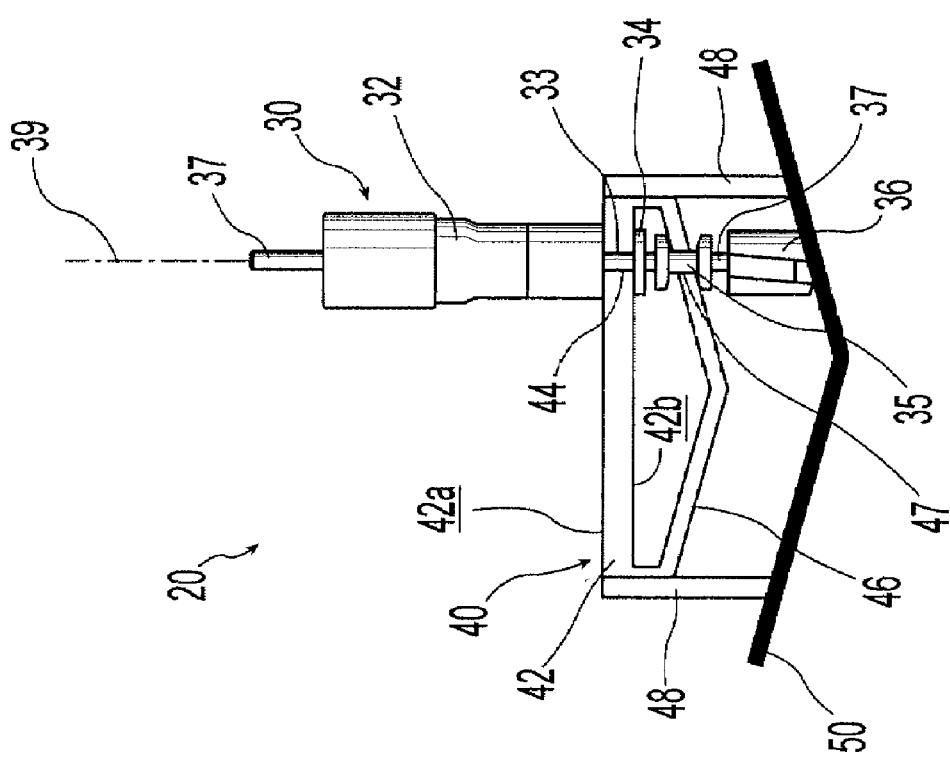
FIG. 2 is another perspective view of the system of FIG. 1.

Referring now to FIGS. 1 and 2, system 20 is shown and generally includes surgical instrument 30 and guide 40. Surgical instrument 30 generally may include first portion or handpiece 32, rotary shaft 37, follower 35, and burr 36. Although surgical instrument 30 is illustrated as a milling instrument, any other suitable surgical instrument may also be utilized with system 20, such as a laser instrument, an ultrasonic instrument, an abrasive water jet instrument, a radiofrequency cautery instrument, an oscillating instrument, or a reciprocating instrument, for example. Surgical instrument 30 may be used to prepare anatomical structure 50 via any suitable process, such as morselizing bone, abrading cartilage, preparing tissue for bone cement, or removing tissue, for example. Guide 40 generally may include top portion 42, guide channel 44 in top portion 42, bottom portion 46, and guide channel 47 in bottom portion 46. Guide 40 may be attached to anatomical structure 50 via supports 48 in any suitable manner.

Handpiece 32 of surgical instrument 30 includes interconnection section 33 which extends through top portion 42 of guide 40 via channel 44. Handpiece 32 further includes guidance structure 34 connected to section 33. When surgical instrument 30 is positioned in guide 40, guidance structure 34 abuts surface 42b of top portion 42 and handpiece 32 abuts surface 42a of top portion 42. The length of section 33 is substantially equal to the thickness of top portion 42 defined between surfaces 42a and 42b and the width of section 33 is substantially equal to the width of channel 44. The abutting relationship of handpiece 32 with surface 42a prevents downward movement, i.e., toward anatomical structure 50, of surgical instrument 30 and the abutting relationship of guidance structure 34 with surface 42b prevents upward movement, i.e., away from anatomical structure 50, of surgical instrument 30. Thus, handpiece 32 of surgical instrument 30 is axially constrained relative to anatomical structure 50 when section 33 is engaged with channel 44. Furthermore, due to the close abutment between handpiece 32 and surface 42a as well as guidance structure 34 and surface 42b, toggle between surgical instrument 30 and guide 40 is substantially eliminated and accuracy is thereby increased.

Rotary shaft 37 includes follower 35 and burr 36 axially fixed thereon. Rotary shaft 37 extends through handpiece 32 and is connected to a rotation-imparting tool (not shown). Rotary shaft 37 and handpiece 32 are joined together via a slip joint (not shown) within handpiece 32. The slip joint provides a rotational linkage, such as a key and keyway configuration, for example, between rotary shaft 37 and handpiece 32. The slip joint allows rotary shaft 37 to vertically translate and move in two dimensions as dictated by bottom portion 46 of guide 40, as described below, while handpiece 32 remains constrained to a single plane of movement by top portion 42 of guide 40. Follower 35 may be formed of an inert and high temperature polyaryletherketone ("PAEK") polymer material, such as polyetheretherketone ("PEEK"), for example.

Referring still to FIGS. 1 and 2, bottom portion 46 of guide 40 substantially matches the shape of a desired surface on anatomical structure 50. For example, bottom portion 46 may be shaped with two generally planar faces with an oblique angle therebetween, as shown in FIGS. 1 and 2. Bottom portion 46 may, however, be formed in any other form, such as a contoured and/or curved shape as well as planar surfaces with multiple facets. Bottom portion 46 includes guide channel 47 formed therein. Guide channel 47 substantially matches the pattern of guide channel 44, described below. Bottom portion 46 defines a track or path for guiding movement of follower 35 of surgical instrument 30 in two dimensions. In an exemplary embodiment, bottom portion 46 defines an undulating track. Advantageously, such an undulating track eliminates the need for a surgeon or user of instrument 30 to replicate the undulating movement required for preparation of anatomical structure 50, as described below.

Figure 3:
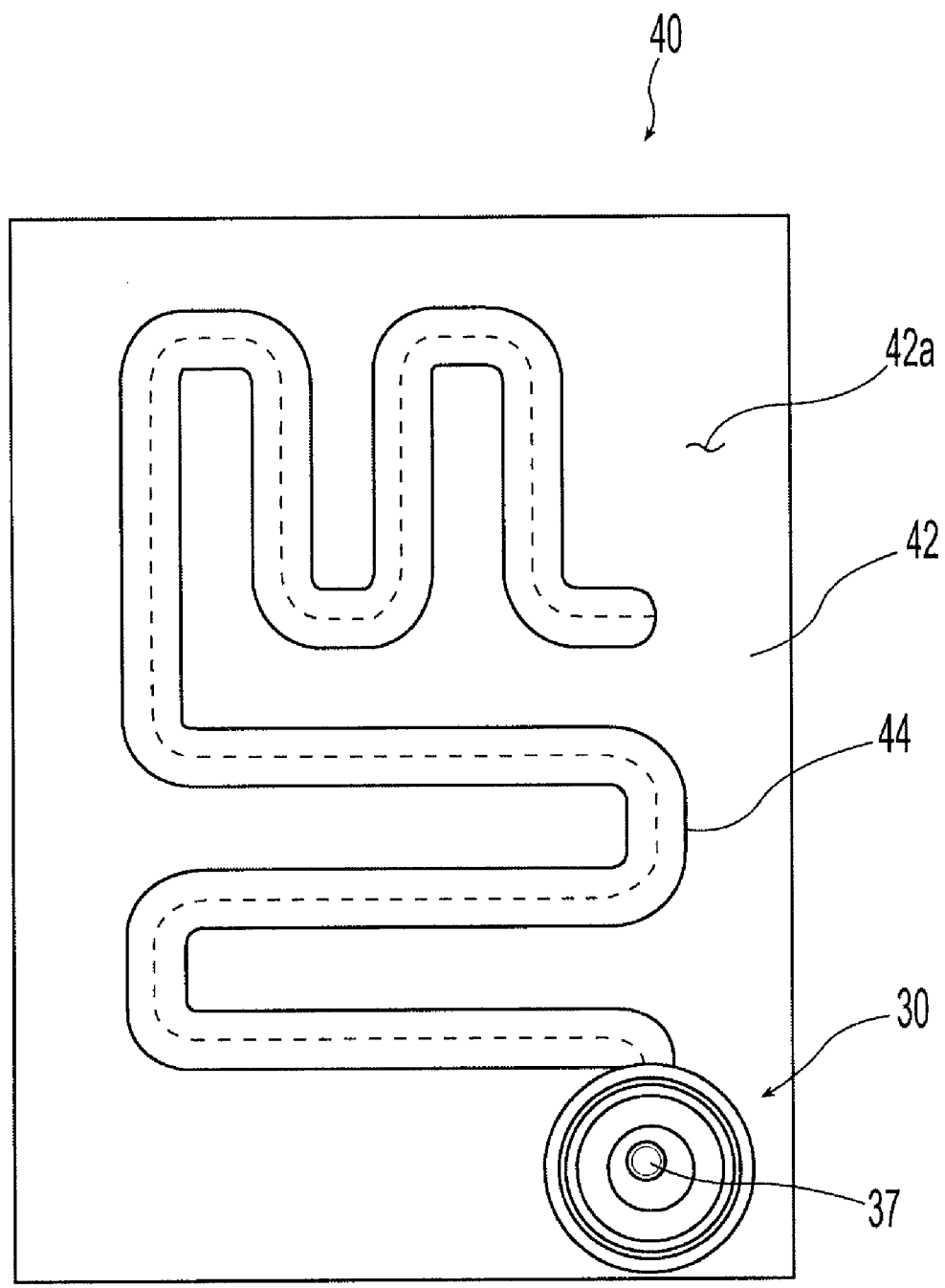
FIG. 3 is a top view of the system of FIG. 1.

Referring now to FIG. 3, top portion 42 of guide 40 is illustrated and includes guide channel 44 formed therein. Guide channel 44 extends through the thickness of top portion 42 from surface 42*a* to surface 42*b* (FIGS. 1 and 2). Guide channel 44 may be formed in any desired shape or pattern depending on the desired surface on anatomical structure 50. Alternatively, guide channel 44 may be a mobile guidance structure, i.e., top portion 42 of guide 40 may be laterally movable relative to anatomical structure 50 with guidance provided by supports 48 to keep top portion 42 in the single plane of movement.

In operation and referring to FIGS. 1-3, a surgeon grasps surgical instrument 30 at handpiece 32. Rotary shaft 37 is connected to the rotation-imparting tool (not shown) to supply rotational motion to burr 36 to effect a milling operation. The surgeon inserts surgical instrument 30 into guide 40 by moving section 33 into guide channel 44 in top portion 42 and by moving follower 35 into guide channel 47 in bottom portion 46. The surgeon then moves handpiece 32 through a pattern of movement dictated by guide channel 44 in a single plane of movement defined by top portion 42 of guide 40. Guide channel 47 matches the pattern of guide channel 44, and, thus, follower 35 also follows the pattern of movement dictated by guide channel 44. Follower 35 tracks the shape of bottom portion 46 of guide 40 in two dimensions for preparing anatomical structure 50. As shown in FIGS. 1 and 2, bottom portion 46 is shaped with two generally planar faces with an oblique angle therebetween. For example, the planar faces of bottom portion 46 define the undulating surface to be prepared on anatomical structure 50. Follower 35 moves or tracks along bottom portion 46 and, consequently, burr 36 follows the same track or path as the shape of bottom portion 46 and removes a portion of anatomical structure 50 to obtain a finish surface on structure 50 which substantially matches the shape of bottom portion 46. Advantageously, the surgeon may select guide 40 to have any desired shape of bottom portion 46 which will be replicated on anatomical structure 50, while simultaneously only requiring movement of handpiece 32 in the single plane of movement. Thus, the surgeon is not required to move handpiece 32 up and down relative to anatomical structure 50 to obtain the finish surface on anatomical structure 50, but, instead the surgeon is required to simply move handpiece 32 in a single plane of movement and follower 35 of surgical instrument 30 tracks bottom portion 46 to dictate the resultant outcome on anatomical structure 50. Burr 36 is axially nondisplaceable relative to follower 35. Thus, as follower 35 follows guide channel 47, burr 36 travels in an identical pattern and direction. Central axis 39 of rotary shaft 37 is shown as perpendicular to surface 42*a* of top portion 42 of guide 40. Alternatively, central axis 39 may form an oblique angle with surface 42*a* or be positioned normal to surface 42*a* in operation, depending on the surgical environment and/or to facilitate a minimally invasive surgical procedure.

In an alternative embodiment illustrated in FIGS. 4 and 4*a*, system 20' includes surgical instrument 30' and a guide (not shown) similar to guide 40, described above with reference to FIGS. 1-3. Surgical instrument 30' is substantially similar and includes the same general components as surgical instrument 30, described above with reference to FIGS. 1-3, except as described below. Surgical instrument 30' may include secondary guide 60 with distal ends 64 and proximal ends 62. Throughout this document, the term "distal" is meant to indicate a portion of the instrument farthest away from a user and the term "proximal" is meant to indicate a portion of the instrument closest to a user. Proximal ends 62 of secondary guide 60 may be positioned in grooves or recesses 38 formed in rotary shaft 37. Recesses 38 may be formed in shaft 37 at predetermined intervals, such as at 1 millimeter (mm) increments, for example. A surgeon may then selectively locate the position of secondary guide 60 on shaft 37 to predetermine the depth of alteration performed by burr 36, as described below. In one embodiment, secondary guide 60 is axially constrained along shaft 37 due to the engagement of proximal ends 62 and recesses 38 but is rotationally independent of rotary shaft 37. Secondary guide 60 may be formed of a material substantially similar to follower 35, described above with reference to FIGS. 1 and 2.

Advantageously, during use of system 20', as described below, secondary guide 60 facilitates constant referencing of anatomical structure 50. Furthermore, secondary guide 60 facilitates a repositioning and shaping of a given anatomical feature on anatomical structure 50. For example, as burr 36 encounters a raised feature on anatomical structure 50, burr 36 initially removes more tissue until burr 36 transitions past the peak of the raised feature after which burr 36 removes less tissue on the downward side of the raised feature. This procedure not only prepares a surface on anatomical structure 50, but the location of the raised feature may be slightly translated, such as for restoring a proper patellar groove angle on a distal femur, for example.

In operation and referring to FIGS. 4 and 4*a*, a surgeon moves surgical instrument 30' in substantially the same manner as described above with reference to the surgical procedure described with respect to FIGS. 1-3. At least one distal end 64 of secondary guide 60 rides on an unprepared surface of anatomical structure 50. Burr 36 extends past secondary guide 60 a distance "x", which is equal to the amount of bone, cartilage, or other tissue to be removed from anatomical structure 50. Advantageously, secondary guide 60 may be displaced along rotary shaft 37 by the surgeon to set a predetermined value of "x". Distal ends 64 allow constant active referencing of unfinished surface 52 of anatomical structure 50 because at least one distal end 64 is always touching unfinished surface 52. Active referencing allows the surgeon to always be aware of the depth of alteration being effected by burr 36 during the surgical procedure, thereby allowing for a more accurate outcome of the surgical procedure. The predetermined amount of tissue removal defined by depth "x" may aid in manufacturing an implant to replace the removed tissue, such as manufacturing a linear thickness cartilage implant/substitute or a flexible hydrophilic polymeric sheet, for example.

In yet another embodiment, guide 40 may be positioned on anatomical structure 50 and/or surgical instrument 30 may be operated with the assistance of a computer assisted surgery (CAS) system. A navigation apparatus of the CAS system may be used to accurately position guide 40 and/or operate surgical instrument 30 by using active or passive tracking, such as optical tracking, electromagnetic tracking, fluoroscopy, radiofrequency tracking, or a coordinate measurement machine, for example.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A system for preparing a surface of an anatomical structure, comprising:
    a surgical instrument, said surgical instrument including a follower and a handpiece having a longitudinal axis, said follower configured for axial movement relative to said handpiece along said longitudinal axis; and
    a guide configured to couple to the anatomical structure, said guide comprising a first track, including a substantially planar portion configured to guide said handpiece within a plane when said handpiece is engaged with said guide, and a second track, configured to guide said follower in at least two dimensions when said follower is engaged with said guide, said second track configured to guide said follower, along said longitudinal axis, independent of the guiding of said handpiece along said longitudinal axis.

2. The system of claim 1, wherein said second track comprises an undulating track.

3. The system of claim 1, wherein said surgical instrument includes a secondary guide.

4. The system of claim 3, wherein said secondary guide includes a distal end positioned a predetermined distance from a distal end of said instrument.

5. The system of claim 3, wherein said secondary guide is configured to be rotationally independent of said surgical instrument.

6. The system of claim 1, wherein said second track substantially defines the surface of the anatomical structure.

7. The system of claim 1, wherein said surgical instrument comprises one of a milling instrument, a laser preparatory instrument, an ultrasonic preparatory instrument, an abrasive water jet instrument, a radiofrequency cautery instrument, an oscillating instrument, and a reciprocating instrument.

8. A system for preparing a surface of an anatomical structure, comprising:
    a surgical instrument comprising a tool and a handpiece; and
    guide means, configured to guide said tool in at least two dimensions and configured to guide said handpiece in one of the at least two dimensions,
    wherein said tool and said handpiece are guided in a first dimension and the tool is further guided in at least one other dimension, independent of movement of said handpiece in the at least one other dimension.

9. The system of claim 8, further comprising secondary guide means for guiding said surgical instrument and for predetermining a depth of the surface of the anatomical structure.

10. A method for preparing a surface of an anatomical structure in two dimensions, comprising the steps of:
    providing or receiving a guide having a first track, including a substantially planar portion, and a second track;
    engaging a handpiece of a surgical instrument with the first track, the handpiece having a longitudinal axis;
    engaging a follower of the surgical instrument with the second track; and
    guiding preparation of the surface in at least two dimensions, including moving the handpiece about the substantially planar portion of the first track and moving the follower about the second track, the second track guiding the follower, along the longitudinal axis, independent of the handpiece movement along the longitudinal axis.

11. The method of claim 10, further comprising the step of providing a secondary guide.

12. The method of claim 11, further comprising the step of adjusting the secondary guide relative to the surgical instrument to predefine a depth of the surface of the anatomical structure.

13. The system of claim 1, wherein said surgical instrument further comprises a tool configured to contact the surface of the anatomical structure, said tool coupled to said guide for axial movement therewith.

14. The system of claim 1, wherein said first and second tracks follow substantially identical paths in a first dimension, said second track differentiating from said first track in a second dimension.

15. The system of claim 8, wherein said guide means guides said handpiece independently of said tool in an axial direction relative to said surgical instrument.

16. The system of claim 8, wherein said guide means guides said tool and said handpiece together in a transverse direction relative to said surgical instrument.

17. The method of claim 10, wherein the guiding step comprises moving a tool of the surgical instrument across the surface of the anatomical structure, the tool coupled to the follower for movement therewith in the two dimensions.

18. The method of claim 17, wherein the guiding step comprises moving the tool axially relative to the handpiece.

19. The method of claim 10, wherein the guiding step comprises moving the handpiece within a plane.

20. The system of claim 1, wherein said first track is stacked on top of said second track, whereby said second track is located nearer the anatomical structure than said first track.

21. The system of claim 1, wherein said first and second tracks are separated by a distance that varies across said guide.

* * * * *